(12) United States Patent
Malnou et al.

(10) Patent No.: US 7,645,444 B2
(45) Date of Patent: Jan. 12, 2010

(54) MULTIPHASE NAIL POLISH

(75) Inventors: Alain Malnou, Routot (FR); Francisco Martinez, Chartres (FR)

(73) Assignee: Fiabila, Maintenon (FR)

( * ) Notice: Subject to any disclaimer, the term of this patent is extended or adjusted under 35 U.S.C. 154(b) by 853 days.

(21) Appl. No.: 10/353,944

(22) Filed: Jan. 30, 2003

(65) Prior Publication Data

US 2003/0165445 A1    Sep. 4, 2003

(30) Foreign Application Priority Data

Jan. 30, 2002    (FR)    ................................... 02 01077

(51) Int. Cl.
  *A61Q 3/00* (2006.01)
  *A61Q 3/02* (2006.01)
(52) U.S. Cl. ....................................................... 424/64
(58) Field of Classification Search ................... 424/64, 424/61
  See application file for complete search history.

(56) References Cited

U.S. PATENT DOCUMENTS

| | | | |
|---|---|---|---|
| 3,483,289 A * | 12/1969 | Michaelson et al. | 424/61 |
| 5,370,866 A | 12/1994 | Frankfurt et al. | |
| 5,607,665 A * | 3/1997 | Calello et al. | 424/61 |
| 5,807,540 A | 9/1998 | Junino et al. | |
| 6,352,686 B2 * | 3/2002 | Bohn et al. | 424/61 |
| 2001/0041168 A1 | 11/2001 | Ramin | |

FOREIGN PATENT DOCUMENTS

| | | |
|---|---|---|
| EP | 0 679 383 | 11/1995 |
| EP | 0 847 751 A1 | 6/1998 |

* cited by examiner

*Primary Examiner*—M P Woodward
*Assistant Examiner*—Melissa S Mercier
(74) *Attorney, Agent, or Firm*—Young & Thompson

(57) ABSTRACT

A nail polish composition comprises a cellulosic filmogenic polymer, a plasticizer and one or more solvents, and is characterized in that it includes 20 to 200% by weight, relative to the cellulosic polymer, of at least one second filmogenic polymer partially insoluble in the cellulosic polymer, giving rise to settling into at least two stable and separate liquid phases at rest. Preferably, the second filmogenic polymer is a vinyl resin, for example polyvinylbutyral. After agitation, this composition has a homogeneous appearance, and can be applied to the nails like a conventional polish.

13 Claims, No Drawings

MULTIPHASE NAIL POLISH

The present invention relates to the field of nail polish, and more particularly to a multiphase nail polish.

Typically, a nail polish composition comprises a principal filmogenic polymer, generally cellulosic, secondary polymers such as polyester resins, acrylic resins or resins of condensation with tosylamide, to improve the physical characteristics of the film, one or several plasticizers to render the principal polymer more flexible and solvents. This basic mixture can also contain coloring materials, suspension agents and additives such as anti-UV agents, moistening agents, low friction agents, hydrating agents, perfumes, etc. . . .

So that these nail polishes will have good cosmetic properties (brilliant, adherent, hard, . . . , it was until now very important that the polymers be compatible with each other, so as to obtain a homogeneous and stable mixture over time without phase loss and without separation, the phase loss being considered as a criterion of poor quality.

However, the inventors have recently produced a nail polish composition, having at rest the form of at least two stable phases which, after agitation, again become homogeneous and can be applied very easily to the nails. After drying, this polish has the properties of a polish of conventional composition.

The composition according to the invention is a nail polish composition, without water, comprising
   a cellulosic filmogenic polymer,
   a plasticizer and
   one or more solvents,
characterized in that it includes 20 to 200% by weight, relative to the cellulosic polymer, of at least one second filmogenic polymer partially insoluble in said cellulosic polymer, giving rise to a separation into at least two stable and separate liquid phases at rest.

Preferably, the cellulosic polymer is nitrocellulose or cellulose acetobutyrate or a mixture of these.

To obtain this stable phase separation, the inventors have found that among the filmogenic polymers partially incompatible with the cellulosic filmogenic polymer or polymers in solution in a mixture of solvents, the vinyl resins are particularly suitable, and more specifically polyvinylbutyral.

Polyvinylbutyral has already been used in various compositions for polish so as to replace:
   either totally nitrocellulose (see U.S. Pat. No. 4,283,324),
   or to replace it partially, but only under conditions in which it would not disturb the homogeneity of the polish (in proportions at which it was "compatible" which is to say "soluble", in other resins, particularly nitrocellulose).

However, in the present case, these vinyl resins, and in particular polyvinylbutyral, permit on the one hand, when the composition is at prolonged rest, to obtain phase separation, and, on the other hand, as soon as this composition is agitated, the latter has a homogeneous appearance and also gives on the nails an entirely uniform appearance.

Preferably, the concentration of this second polymer is greater than about 3% by weight of the total composition of the polish.

The preferred proportions of the second filmogenic polymer are 80 to 200%, preferably 120 to 180%, by weight, of the cellulosic polymer.

The solvent (or mixture of solvents) is a solvent both for the first filmogenic polymer (cellulosic), and of the second polymer partially incompatible with the first. It also permits adjusting the phase separation between the two solutions of polymer.

The solvent or the mixture of solvents is selected from aliphatic compounds such as acetates, ketones, alcohols, alkanes or a mixture of these, and more particularly from among ethyl acetate, butyl acetate, propyl acetate, isobutyl acetate, ethanol, propanol, isopropanol, butanol, methylethylketone, methylisobutylketone, heptane and hexane, and mixtures of these.

There are thus obtained two phases that are perfectly clear and stable with time. The height of these phases varies with the polymers, their proportions and with the solvents used. After agitation, these two phases give a homogeneous mixture which has the same properties as a conventional composition.

Such a solvent or mixture of solvents permits, when the polish is agitated, to promote a very fine emulsion of the filmogenic polymers with each other, and to prevent, during drying, precipitation of one of the polymers, which would impede good adherence of the polish to the nails.

The composition according to the invention can also include one or several coloring materials selected from pigments, soluble colorants, particularly conventional colorants used in cosmetics, and so-called decorative particles, such as nacres or flakes.

The inventors have also discovered that the coloring materials dispersed in one of the polymers, such as pigments, remains exclusively in one of the phases, the one including the cellulosic filmogenic polymer. On the contrary, colorants in solution are distributed in the two phases in a substantially equivalent manner.

This phenomenon permits obtaining a composition of multiphase nail polish, having at rest at least two stable phases, which can be of different colors, particularly if the cellulosic phase contains a pigment.

The composition can also contain colored particles which, after sedimentation, give rise to a third color layer, smaller, in the bottom of the bottle.

There is thus obtained in the bottle, at rest, a nail polish with several layers, colored by means of coloring materials which are either in suspension or dispersed in cellulosic polymer, or in solution, respectively coloring the bottom of the bottle, the lower phase or the upper phase of the polish.

After homogenization, the composition according to the invention described above can be used for application to the nails as a nail polish alone, as a finish polish or as an intermediate layer.

The present invention is illustrated by the examples of embodiments of multiphase nail polish given hereafter (the numbered indications are the percentages by weight of the total composition).

EXAMPLE 1

The following constituents are mixed under the usual conditions of preparation of nail polish.

| | |
|---|---|
| Nitrocellulose 70% in isopropanol | 7.6 |
| Plasticizer | 2.2 |
| Thermoplastic acrylic resin | 4.9 |
| Polyvinylbutyral | 8.3 |
| Ethyl acetate | 44 |
| Butyl acetate | 28 |
| Heptane | 5 |

Polyvinylbutyral is partially incompatible with nitrocellulose in this mixture of solvents. At rest, this composition undergoes separation into two phases, of equivalent volumes, perfectly clear. The lower phase is rich in nitrocellulose and the upper phase is rich in vinyl resin.

If there is added to this composition a colorant soluble in the mentioned solvents, the color is distributed uniformly over the two phases.

EXAMPLE 2

In the composition according to claim 1, there is added a dispersion of Bentone®, a red pigment, in the form of particles and a solution of colorant in the proportions indicated below. The dispersions of Bentone and of colored pigment are ground into the solution of nitrocellulose+plasticizer.

| | |
|---|---|
| Nitrocellulose 70% in isopropanol | 7.4 |
| Plasticizer | 2.1 |
| Thermoplastic acrylic resin | 4.7 |
| Polyvinylbutyral | 8 |
| Ethyl acetate | 43 |
| Butyl acetate | 27 |
| Bentone | 0.3 |
| Red 7 Ca lake | 0.3 |
| Titanium mica/Yellow iron oxide | 2 |
| Solution of blue colorant | 0.5 |

As in the preceding example, there is noted at rest two phases of equal volume proportions.

As the composition is not strongly "jelled", the particles of mica/titanium/yellow iron oxide settle out, and form a third layer at the bottom of the bottle.

The red pigment is distributed in a uniform manner, exclusively in the lower liquid phase rich in nitrocellulose.

The blue colorant is distributed in the three phases, but as its coloring power is weak, it is visible only in the upper transparent liquid phase.

There is thus obtained in the bottle at rest, a polish in three phases: a small solid yellow deposit at the bottom of the bottle, then a red phase and an upper blue phase.

After homogenization by agitation, there is obtained in the bottle a red composition with orange reflections like the film obtained on the nails after application.

The de-mixing time (settling) being several hours, the composition remains homogeneous for the duration of its application to the nails and during its drying.

This composition has, on the nails, the same properties as a conventional polish.

The invention claimed is:

1. A nail polish composition, without water, comprising nitrocellulose;
    a plasticizer;
    one or more solvents; and
    polyvinylbutyral,
characterized in that
    the nail polish composition is a multiphase composition,
    the polyvinylbutyral is partially insoluble in the nitrocellulose, and
    polyvinylbutyral is present in an amount of 120 to 200% by weight, relative to the nitrocellulose so that the nail polish composition settles into a multiphase composition of at least two stable and separate liquid layers at rest.

2. The composition according to claim 1, further comprising cellulose acetobutyrate mixed with the nitrocellulose.

3. The composition according to claim 1, characterized in that the amount of polyvinylbutyral is greater than 3% by weight of the total composition of the polish.

4. The composition according to claim 1, characterized in that polyvinylbutyral is 120 to 180% by weight of the nitrocellulose.

5. The composition according to claim 1, characterized in that the solvent or solvents are aliphatic compounds selected from the group consisting of acetate, ketones, alcohols, alkanes and mixtures thereof.

6. The composition according to claim 5, characterized in that the solvent or solvents are selected from the group consisting of ethyl acetate, butyl acetate, propyl acetate, isobutyl acetate, ethanol, propanol, isopropanol, butanol, methylethylketone, methylisobutylketone, heptane and hexane, and mixtures thereof.

7. The composition according to claim 1, further comprising one or several coloring materials selected from the group consisting of pigments, soluble colorants, decorative particles, nacres, and flakes.

8. A method of applying the composition according to claim 1, after homogenization, comprising applying said composition to nails as a nail polish, as a finishing polish or as an intermediate layer.

9. The composition according to claim 1, wherein said at least two stable and separate liquid layers are homogenized, and wherein said composition can be applied to nails as a nail polish, as a finishing nail polish, or as an intermediate layer.

10. The composition according to claim 1, wherein said at least two stable and separate liquid layers comprise different coloring materials.

11. The composition according to claim 10, wherein said at least two stable and separate liquid layers, when homogenized, form a composition of a uniform appearance.

12. A nail polish composition without water, comprising:
    a first phase comprising nitrocellulose, solvent and plasticizer;
    a second phase comprising polyvinylbutyral and a solvent, wherein,
    the polyvinylbutyral is partially insoluble in the nitrocellulose;
    the polyvinylbutyral is present in amount of 120 to 200% by weight relative to the nitrocellulose,
    the phases form at rest, separate and stable layers, and give with agitation a nail polish ready to apply.

13. The nail polish composition according to claim 12, wherein,
    the first phase further comprises at least one coloring material, and
    the coloring material remains in only one layer at rest after agitation of the composition.

* * * * *

UNITED STATES PATENT AND TRADEMARK OFFICE
CERTIFICATE OF CORRECTION

PATENT NO. : 7,645,444 B2  
APPLICATION NO. : 10/353944  
DATED : January 12, 2010  
INVENTOR(S) : Malnou et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1386 days.

Signed and Sealed this

Twenty-first Day of December, 2010

David J. Kappos  
*Director of the United States Patent and Trademark Office*